(12) United States Patent
Kilburn et al.

(10) Patent No.: US 7,708,739 B2
(45) Date of Patent: May 4, 2010

(54) CONTROLLED FORCE IMPACTING DEVICE (75) Inventors: Randy Kilburn, Warsaw, IN (US);
Barry Schneiders, Plymouth, IN (US);
Dennis Cassell, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 190 days.

(21) Appl. No.: 11/094,929

(22) Filed: Mar. 31, 2005

(65) Prior Publication Data
US 2006/0241631 A1 Oct. 26, 2006

(51) Int. Cl.
*A61F 5/00* (2006.01)
(52) U.S. Cl. .................................... 606/86 R
(58) Field of Classification Search .............. 606/86, 606/89, 91, 100, 99; 623/22.11–23.38
See application file for complete search history.

(56) References Cited

U.S. PATENT DOCUMENTS

| | | | |
|---|---|---|---|
| 2,421,354 A | 5/1947 | Reiter | |
| 2,437,014 A * | 3/1948 | Arnesen et al. | 606/100 |
| 2,725,878 A * | 12/1955 | Reiter | 606/79 |
| 2,960,864 A | 11/1960 | Watts | |
| 3,210,836 A | 10/1965 | Johanson et al. | |
| 4,653,486 A | 3/1987 | Coker et al. | |
| 4,919,216 A | 4/1990 | Ikegami | |
| 5,037,424 A | 8/1991 | Aboczsky | |
| 5,116,339 A | 5/1992 | Glock | |
| 5,169,399 A | 12/1992 | Ryland et al. | |
| 5,171,243 A | 12/1992 | Kashuba et al. | |
| 5,431,657 A | 7/1995 | Rohr | |
| 5,571,200 A | 11/1996 | Cohen et al. | |
| 5,584,837 A * | 12/1996 | Petersen | 606/91 |
| 5,735,855 A | 4/1998 | Bradley et al. | |
| 5,741,268 A | 4/1998 | Schuetz et al. | |
| 6,370,993 B1 | 4/2002 | Pitstick | |
| 7,121,165 B2 * | 10/2006 | Yamakawa | 81/6 |
| 2004/0064145 A1 | 4/2004 | Ball et al. | |
| 2006/0253120 A1 * | 11/2006 | Anderson et al. | 606/86 |

FOREIGN PATENT DOCUMENTS

EP 1 190 697 3/2002

* cited by examiner

*Primary Examiner*—Thomas C Barrett
*Assistant Examiner*—Nicholas Woodall
(74) *Attorney, Agent, or Firm*—Maginot, Moore & Beck LLP (57) ABSTRACT An impacting tool includes a trigger mechanism that is activated when a predetermined amount of energy is stored in the impacting tool. When the impacting tool is activated, the stored energy is precipitously discharged through an impact rod which is configured to transfer a controlled force to an orthopaedic component.

14 Claims, 6 Drawing Sheets

CONTROLLED FORCE IMPACTING DEVICE

FIELD OF THE INVENTION

The present invention relates to impacting devices, such as those used to provide impact force to a prosthetic component in order to secure the prosthetic component to another device or to tissue.

BACKGROUND OF THE INVENTION

Many orthopaedic procedures involve the implantation of prosthetic devices to replace badly damaged or diseased bone tissue. Common orthopaedic procedures that involve prosthetic devices include total or partial hip, knee and shoulder replacement. For example, a hip replacement often involves a prosthetic femoral implant. The femoral implant usually includes a rigid stem that is secured within the natural femur bone tissue. The femoral implant further includes a rounded head that is received by, and may pivot within, a natural or artificial hip socket. Shoulder replacement is somewhat similar, and typically includes a humeral implant that includes a rigid stem and a rounded head. The rigid stem is secured within the natural humerus bone tissue and the rounded head is pivotally received by a shoulder socket.

Increasingly, prosthetic devices are provided as subcomponents that are assembled during surgery. In particular, the different anatomies of different patients require that prosthetic devices such as femoral and humeral implants be available in different sizes and configurations. By way of simplified example, a humeral implant may be available in as many as six or more humeral head diameters. Stems may similarly vary in size and/or in shape. Because the appropriate overall configuration of the implant can typically only be determined during the surgical procedure, it is advantageous that many configurations and sizes of implants be at the disposal of the surgeon. Instead of providing a separate implant for each possible combination of features, implants are provided as modular kits of subcomponents that allow the surgeon to mix and match different subcomponents to achieve the most advantageous combination for the patient. Thus, the surgeon can pick from several sizes or configurations of each component and combine the components to form an implant having an optimal combination of features.

Figures 1, 2, 3:
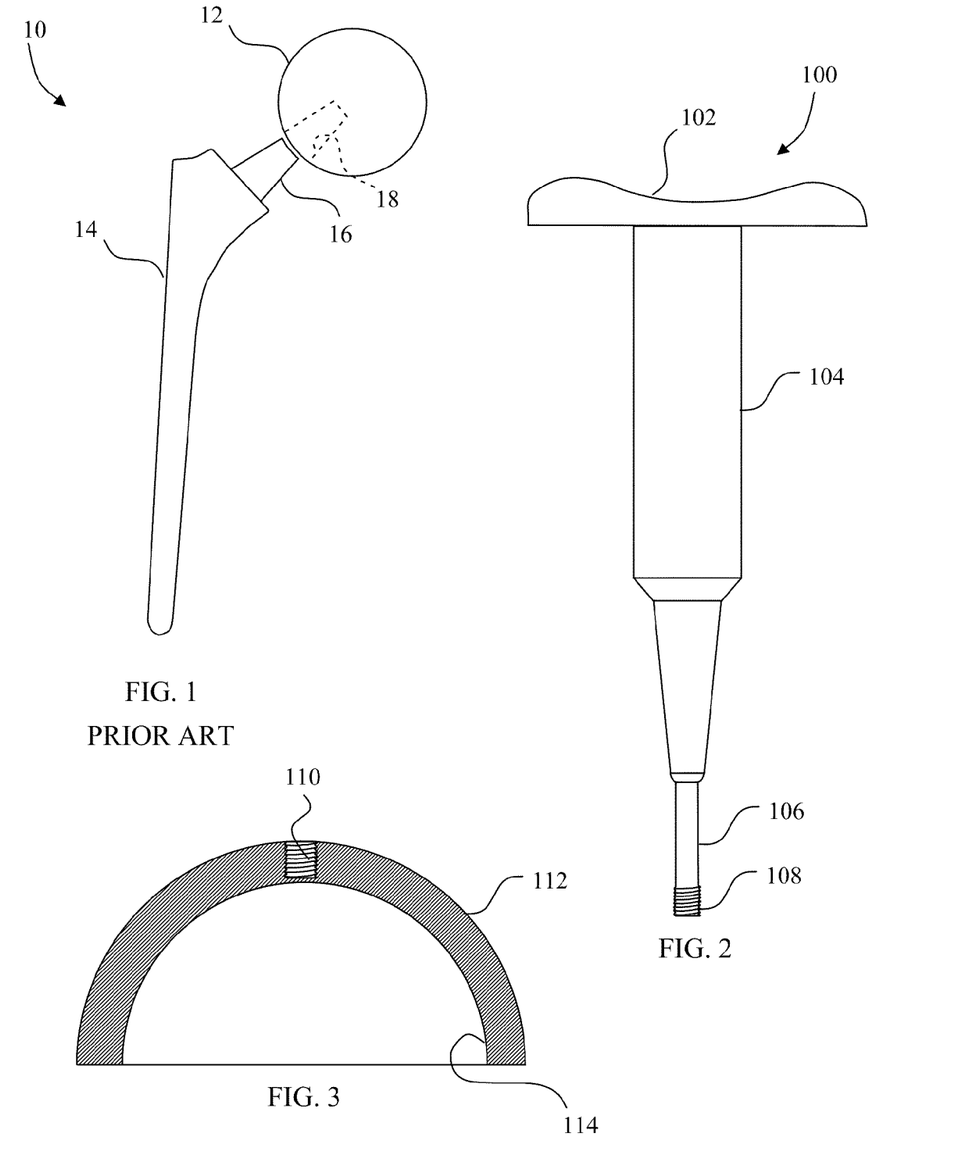
FIG. 1 shows a side plan view of a prior femoral implant that employs a Morse taper.
FIG. 2 shows a side plan view of an exemplary controlled force impacting tool according to the present invention.
FIG. 3 shows a side cross-sectional view of an impacting tip that is engageable with the impacting tool of FIG. 2.

One example of a modular implant is the femoral implant 10 shown in FIG. 1. The femoral implant 10 includes a femoral head 12 that may be assembled onto a femoral stem 14. The femoral stem 14 is configured to be implanted in the intramedullary tissue of a natural femoral bone, while the femoral head 12 is configured to be received into an acetabular cup implanted into the acetabulum. The femoral stem 14 includes a tapered plug 16 that is designed to be received by a tapered receptacle 18 in the femoral head 12. It can be appreciated that the surgeon may secure alternative femoral head designs on the same femoral stem 14, thus providing the surgeon with a broad array of femoral head size options.

Once the components are selected, such as the femoral head 12 and the femoral stem 14 of FIG. 1, then the components are assembled either externally or in vivo. A popular method of securing implant components together involves the use of a Morse taper. The components of FIG. 1 by way of example include a Morse taper arrangement. In particular, a Morse taper is a feature in which a tapered male component, e.g. the tapered plug 16, is received into a tapered female component, e.g. the receptacle 18. The taper angle of the plug 16 is preferably, but need not be, slightly less than the taper angle of the receptacle 18. In use, the plug 16 advances into the receptacle 18 until it begins to engage the receptacle 18. The further into the receptacle the plug 16 is forced, the more tightly it engages.

The force applied to secure the plug 16 within the receptacle 18 is proportional to the retention force of the plug 16 within the receptacle 18. Thus, if a sufficient amount of force is applied, then the femoral head 12 will be securely fastened on the femoral stem 14. Other prosthetic devices employ Morse tapers for substantially the same reasons.

To apply sufficient force to lock the Morse taper arrangement, it is known to impact the femoral head 12 such that the impact force directs the femoral head 12 toward the femoral stem 14. The impact force drives the plug 16 into the receptacle 18 and forms the Morse taper lock. A hammer or mallet is typically struck directly on the head 12, or through an impacting plate, tool or mechanism.

Previously, the surgeon (or other person) would impact a prosthetic implant several times without knowing if the necessary force had been applied to lock the Morse taper sufficiently. Often, in order to be sure that the Morse taper had locked, the surgeon or assistant would use excessive force. The use of excessive force is undesirable because of the potential for damage to the bone tissue or the implant device.

Although some surgeons have developed a feel or instinct as to the amount of force that is needed to form a Morse taper lock when dealing with replacement components made from more traditional materials such a cobalt chrome, there is a relatively recent movement toward the use of ceramic replacement components. While providing many benefits over replacement components made from, for example, cobalt chrome, the ceramic components are generally more brittle. Accordingly, even surgeons adept at forming Morse taper locks using materials such as cobalt chrome may use excessive force when attempting to form a Morse taper lock with a ceramic replacement part.

Thus, there is a need for assisting surgical personnel in ensuring that sufficient force has been applied to a Morse taper to lock the Morse taper while avoiding excessive force. Such need is widespread as Morse tapers have commonly been used for connection of many types of implant devices. Moreover, there is a need for assisting surgical personnel in determining whether sufficient force has been applied to a Morse taper to lock the Morse taper when the replacement components are made from different materials. There is further a need for ensuring that sufficient force has been applied to a Morse taper to lock the Morse taper for replacement components of different sizes.

SUMMARY OF THE INVENTION

The present invention provides some of the above needs, as well as others, by providing a controlled force impacting tool. In particular, the impacting tool of the present invention includes a trigger mechanism that is activated when a predetermined amount of energy is stored in the impacting tool. When the impacting tool is activated, the stored energy is precipitously discharged through an impact rod which is configured to transfer the impacting force to an orthopaedic component.

If the features and/or the other structures of the tool are chosen such that the stored energy corresponds to an amount of force needed to lock a Morse taper, then a surgeon may use the impact tool to impact a device having a Morse taper and be assured that sufficient force has been applied when the stored energy is discharged through the impacting rod. Moreover, the tool ensures that excessive force is not applied. Thus, the impacting tool of the present invention provides a controlled force for impaction of an orthopaedic component.

A first embodiment of the invention is an impacting device that includes a housing with a centering hole. An impacting piston that includes a central bore with a closed end is located within the housing above the centering hole. A push rod is located below the centering hole and includes a stem that projects through the centering hole. A biasing spring biases the stem laterally away from the central bore. The distal end of the push rod is curved complimentarily with the curved proximal end of an impacting rod. The impacting rod extends to a location outside of the housing. The distal end of the impacting rod is configured to engage an impacting tip.

A handle allows an impacting spring which is located above the impacting piston to be compressed against the impacting piston. Triggering of the impacting tool is accomplished by compressing the impacting spring until a shoulder region of the push rod is forced against the wall of the centering hole which causes the stem to align with the central bore. The impacting piston is then accelerated toward the stem by the impacting spring and a controlled force is transferred through the push rod and the impacting rod to the impacting tip.

In accordance with an alternative embodiment, an impacting tool with a housing includes an impacting spring located above an impacting piston. A push rod is located between the impacting piston and an impacting rod which is configured to engage an impacting tip. The impacting piston includes a central bore with a closed end. A biasing spring biases a stem of the push rod laterally away from the central bore. A handle is positioned above the impacting spring and includes trigger arms extending away from the handle.

As the handle is forced toward the impacting rod, the impacting spring is compressed. The trigger arms cooperate with a collar on the push rod to trigger the impacting tool when a predetermined amount of energy is stored in the impacting tool. Specifically, as the collar is seated on the trigger arms, the stem is forced laterally into alignment with the central bore. The impacting piston is then accelerated toward the stem by the impacting spring and when the closed end of the central bore impacts the stem, a controlled force is transferred through the push rod and the impacting rod to the impacting tip.

Impacting tips may be provided in the form of a kit wherein each of a plurality of impacting tips is configured to mate with a different orthopaedic component. In one embodiment, an impacting tip includes a curvilinear internal cavity configured to mate with a portion of an orthopaedic component such as the head of a femoral component.

In accordance with another alternative embodiment of the invention, an impacting tool comprises a plunger operable to compress an impacting spring against an impacting piston. Trigger arms extending upwardly within the housing of the impacting tool are constrained in a first position by projections on plunger. In the first position, the trigger arms maintain the impacting piston above a portion of the trigger arms as the impacting spring is being compressed by the plunger. When a predetermined amount of energy has been stored in the impacting spring, the trigger arms are no longer constrained by the projections and move to a second position. In the second position, the impacting piston is allowed to pass the portion of the trigger arms and the impacting spring accelerates the impacting piston toward an impacting rod. The impacting force is transferred from the impacting piston to the impacting rod when the impacting piston impacts the impacting rod.

In this embodiment, the impacting rod is integrally formed with an impacting tip. The controlled force from the impacting piston is transferred through the impacting rod to an orthopaedic component through the impacting tip. In accordance with a further embodiment, a plurality of impacting tools are provided in a kit wherein each of the plurality of impacting tools includes an impacting tip of a size different than the impacting tips of the other of the plurality of impacting tools.

The above embodiments may be used to ensure that sufficient force has been applied to lock a Morse taper arrangement. As such, the above embodiments provide the advantage of reducing the tendency to use undesired excessive force. Moreover, the above embodiments may be implemented relatively simply and inexpensively. The controlled force impact tool and method may further be used for other surgical purposes in which impact force is advantageously limited, such as for assembling components that employ non-Morse taper connecting features.

The above described features and advantages, as well as others, will become more readily apparent to those of ordinary skill in the art by reference to the following detailed description of certain embodiments of the invention and accompanying drawings.

DETAILED DESCRIPTION

FIG. 2 shows a controlled force impacting tool 100 according to the invention having a contoured handle 102 and a housing 104 extending therefrom. An impacting rod 106 extends forwardly of the housing 104. The impacting rod 106 includes a threaded distal end 108 that engages a threaded portion 110 of an appropriate impacting tip 112 as shown in FIG. 3. The impacting tip 112 includes a curvilinear internal cavity 114 conformed to mate with a replacement component such as the femoral head 12. In accordance with the present invention, a plurality of impacting tips may be provided, such as in a kit. Each of the plurality of impacting tips may be configured to mate respectively with one of a plurality of replacement components of different types and of different sizes.

Figure 4:
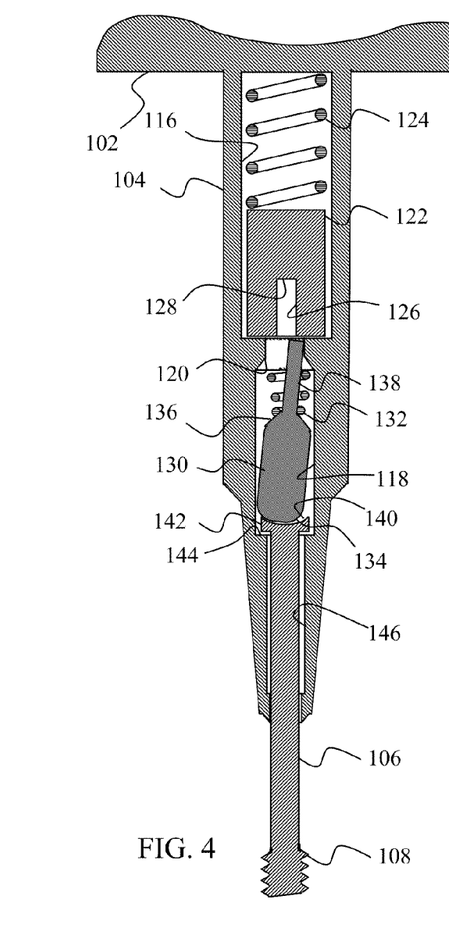
FIG. 4 shows a side cross-sectional view of the impacting tool of FIG. 2.
Figure 5:
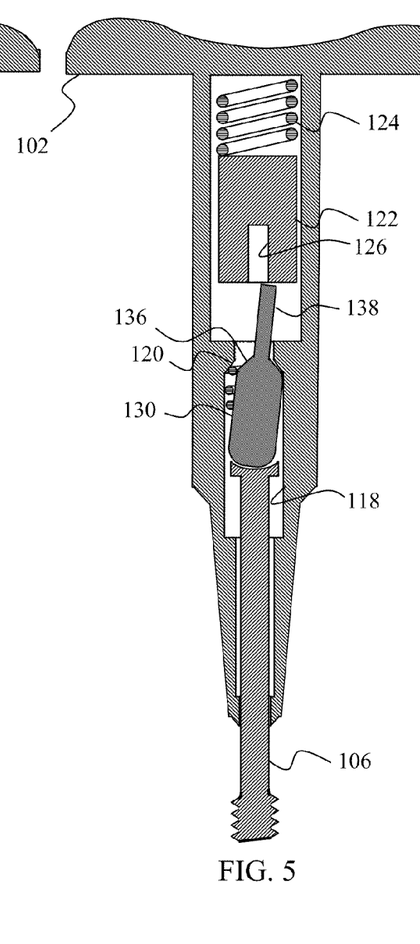
FIG. 5 shows a side cross-sectional view of the impacting tool of FIG. 2 with the impacting spring in a compressed condition.
Figure 6:
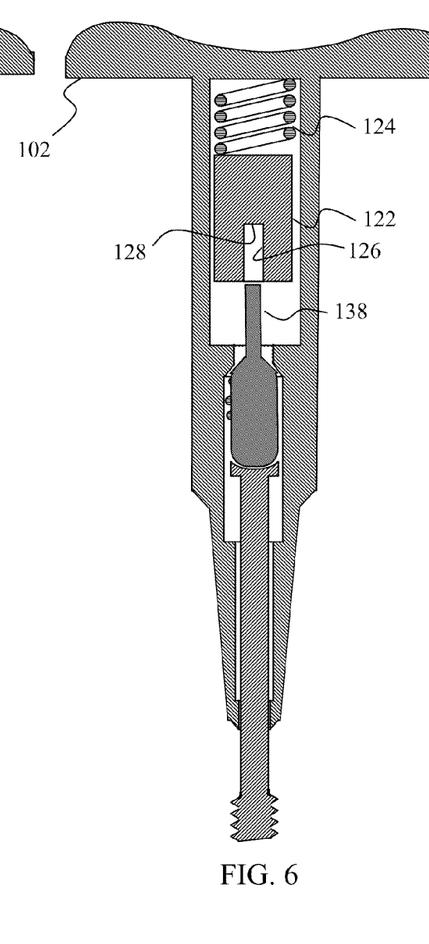
FIG. 6 shows a side cross-sectional view of the impacting tool of FIG. 5 in a triggered condition.

The internal components of the impacting tool 100 are best seen in FIGS. 4-6. The housing 104 is hollow. An impacting spring compartment 116 is separated from a push rod compartment 118 by a centering hole 120. An impacting piston 122 is disposed adjacent to an impacting spring 124 within the impacting spring compartment 116. The impacting piston 122 includes a central bore 126 with a closed end 128.

A push rod 130 and a biasing spring 132 are disposed within the push rod compartment 118. The push rod 130 includes a rounded distal end 134, a shoulder region 136 and a stem 138. The stem 138 is configured to pass through the centering hole 120 and to fit within the central bore 126 as is discussed more fully below. The rounded distal end 134 of the push rod 130 is configured to contact the rounded proximal end 140 of the impacting rod 106. The biasing spring 132 is configured such that when there is no force being applied to the contoured handle 102, the stem 138 is biased toward a position outside of the central bore 126. The biasing spring 132 further biases the stem 138 laterally away from the central bore 126 toward a solid portion of the distal end of the impacting piston 122 as shown in FIG. 6.

The rounded proximal end 140 and a collar 142 of the impacting rod 106 are also located within the push rod compartment 118. The collar 142 cooperates with a ledge 144 in the housing 104 to maintain the rounded proximal end 140 of the impacting rod 106 within the push rod compartment 118. The impacting rod 106 extends from within the push rod compartment 118 through a bore 146 formed in the housing 104 to a position forward of the housing 104.

Turning to the operation of the embodiment of the invention shown in FIG. 2, the replacement components to be joined together are positioned so that, in the case of a Morse taper lock, the plug of a first component is located snugly within the receptacle of a second component. The appropriate impacting tip such as the impacting tip 112 is then selected and mounted on the threaded distal end 108 of the impacting rod 106. The impacting tip is selected such that a large surface area of the internal cavity 114 of the impacting tip 112 will contact the component to be driven. Of course, other modes of engaging impacting tips with the impacting rod are contemplated within the scope of the present invention in addition to modes using threaded engagement. Such modes include, but are not limited to, modes used to provide so-called "quick disconnect" engagement.

Next, the impacting tip 112 is placed in position over the component to be driven. At this point, the impacting tool 100 is in the condition shown in FIG. 4. Thus, the impacting spring 124 is fully extended and the impacting piston 122 is at the distal end of the impacting spring compartment 116. Since there is no pressure applied to the contoured handle 102, the biasing spring 132 is also fully extended both axially and laterally with respect to the axis of the impacting tool 100. Thus, the push rod 130 is forced against the impacting rod 106 with the collar 142 against the ledge 144 of the housing 104.

With the biasing spring 132 fully extended, the stem 138 extends through the centering hole 120 but is maintained outside of the central bore 126 of the impacting piston 122. The biasing spring 132 further biases the stem 138 about 10 to 15 degrees off of the centerline of the centering hole 120. In this position, the stem 138 is adjacent to a solid portion of the distal end of the impacting piston 122.

The impact tool 100 is operated by forcing the contoured handle 102 toward the impacting tip 112 so as to begin to compress the biasing spring 132. This causes the impacting rod 106 to be forced against the push rod 130. More precisely, the rounded proximal end 140 of the impacting rod 106 is forced against the rounded distal end 134 of the push rod 130. Even though the impacting rod 106 and the push rod 130 are not aligned because of the bias exerted on the push rod 130 by the biasing spring 132, solid contact between the impacting rod 106 and the push rod 130 is provided because both the rounded proximal end 140 of the impacting rod 106 and the rounded distal end 134 of the push rod 130 are complimentarily rounded.

Because the proximal end of the stem 138 is not aligned with the central bore 126 of the impacting piston 122, continued pushing on the contoured handle 102 forces the stem 138 against the distal end of the impacting piston 122 which in turn begins to compress the impacting spring 124. Of course, any suitable mechanism could be used to compress the impacting spring such as, but not limited to, directly pulling the impacting spring into a compressed condition. As the impacting spring 124 is compressed, more of the impacting rod 106 is forced into the housing 104 as the contoured handle 102, the push rod 130 and the impacting piston 122 are forced toward the impacting tip 112. This continues until the impacting tool 100 is in the condition shown in FIG. 5.

In FIG. 5, the shoulder region 136 of the push rod 130 is not in contact with the sides of the centering hole 120. Thus, stem 138 is still forced against the impacting piston 122 and the push rod 130 is canted within the push rod compartment 118. The impacting spring 124 is in a compressed condition, with a large amount of energy stored in the impacting spring 124 due to the compression. As the surgeon continues to press upon the contoured handle 102, the shoulder region 136 is forced against the side of the centering hole 120.

The shoulder region 136 and the centering hole 120 are formed such that as the shoulder region 136 is forced against the side of the centering hole 120, the push rod 130 will become aligned with the centering hole 120. In the embodiment of FIG. 5, this is accomplished by forming both the shoulder region 136 and the side of the centering hole 120 in the shape of complimentary frustums. As the push rod 130 is aligned with the center hole 120, the stem 138 of the push rod 130 is forced laterally toward the central bore 126 of the impacting piston 122. As the shoulder region 136 becomes seated on the side of the centering hole 120, the stem 138 is brought into alignment with the central bore 126 as shown in FIG. 6.

Since the stem 138 is aligned with the central bore 126 of the impacting piston 122, the impacting spring 124 is no longer being forced into compression by the force applied to the contoured handle 102. This is referred to herein as a "triggered condition". Accordingly, the impacting spring 124 is allowed to release the energy stored by compression of the impacting spring 124 and to accelerate the impacting piston 122 toward the push rod 130. Thus, in this embodiment, the shoulder region 136 of the push rod 130 in combination with the side of the centering hole 120 comprise a trigger mechanism which may be used to release the energy stored within the impacting spring 124. Of course, other centering devices, such as a ramp or a lever, or other release mechanisms could be used as a trigger mechanism.

Because the stem 138 is longer than the depth of the bore 126, the first contact between the push rod 130 and the impacting piston 122 after the impact tool is triggered occurs when the closed end 128 of the central bore 126 impacts the stem 138. As the closed end 128 of the central bore 126 impacts the stem 138, force in the form of the momentum of the impacting piston 122 and some residual compression of the impacting spring 124 is transferred to the push rod 130. This force is in turn transferred to the impacting rod 106 and then to the impacting tip 112 and into the component being impacted.

The impact tool 100 may then be removed from the component being impacted. This allows the biasing spring 132 to force the push rod 130 axially toward the distal end of the impacting tool 100. As the push rod 130 moves, the stem 138 will be moved completely outside of the central bore 126 of the impacting piston 122. At this point, the biasing spring 132 further forces the stem 138 in a lateral direction, moving the stem 138 out of alignment with the central bore 126 and resetting the impacting tool 100 for another cycle.

As may be appreciated from the foregoing description, the amount of force transferred to the impacting rod 106 is the result of certain variables which may be selected to provide the desired force for a particular impaction. For example, the spring constants of the impacting spring and the biasing spring both contribute to the amount of energy transferred to the impacting rod. Additionally, the mass of the impacting piston and the depth of the central bore and the length of the stem on the push rod affect the amount of momentum that is generated and subsequently transferred to the impacting rod. Accordingly, a wide variety of impacting tool configurations are provided according to the present invention.

Additionally, the impacting tool can be made in any suitable size. In one configuration, the impacting tool may be the size of a syringe and the contoured handle may be configured to receive a thumb to allow for use with one hand. In another embodiment, the impacting tool may be large enough to be provided with a hand grip around the housing while the contoured handle is configured to be pressed with the palm of a user.

Of course, the final amount of force transferred to the orthopaedic component will also vary according to certain variables which in this embodiment are not considered design variables. By way of example, the rapidity with which the impacting spring in the embodiment of FIG. 2 is being compressed at the moment of triggering will have some affect on the final amount of impacting force that is transferred to the orthopaedic component. Nonetheless, by selection of the above discussed design variables, even allowing for some non-design variables, the amount of force that is transferred to the orthopaedic component is sufficiently controlled. Thus, a force that is sufficient to produce the desired effect while minimizing excessive force, that is, a controlled force, is transferred to the orthopaedic component.

Figure 7:
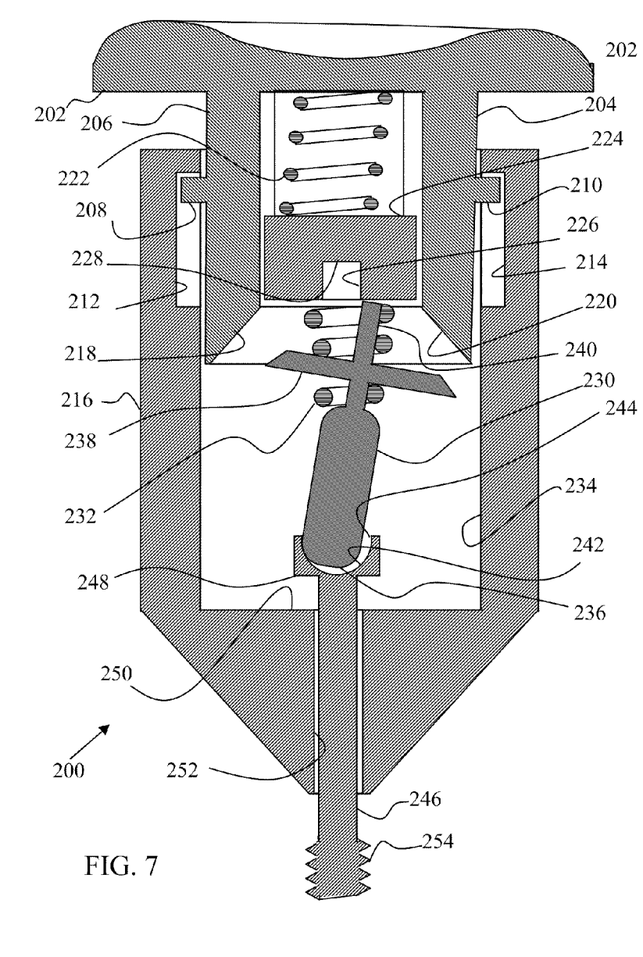
FIG. 7 shows a side cross-sectional view of an alternative controlled force impacting tool according to the present invention.

Referring now to FIG. 7, an alternative controlled force impacting tool 200 according to the invention includes a contoured handle 202 with two triggering arms 204 and 206 extending therefrom. The triggering arms 204 and 206 include stubs 208 and 210 which are movably located within grooves 212 and 214, respectively, of outer housing 216. At the distal end of the triggering arms 204 and 206 are beveled shoulders 218 and 220, respectively.

An impacting spring 222 is located between the triggering arms 204 and 206 and beneath the contoured handle 202 as shown in FIG. 7. An impacting piston 224 is located at the distal end of the impacting spring 222. The impacting piston 224 includes a central bore 226 with a closed end 228.

A push rod 230 and a biasing spring 232 are disposed within a push rod compartment 234 formed by the outer housing 216. The push rod 230 includes a rounded distal end 236, a beveled collar 238 and a stem 240. The stem 240 is configured to fit within the central bore 226 as is discussed more fully below. The biasing spring 232 is fixedly attached to the push rod 230 at one end and to the impacting piston 224 at the other end. The biasing spring 232 is configured such that when there is no force being applied to the contoured handle 202, the stem 240 is biased axially toward a position outside of the central bore 226. The biasing spring 232 further biases the stem 240 laterally away from the central bore 226 toward a solid portion of the distal end of the impacting piston 224.

The rounded distal end 236 of the push rod 230 is configured to contact the rounded end 242 of a retaining well 244 on the impacting rod 246. The impacting rod 246 includes a collar 248 that cooperates with a ledge 250 in the outer housing 216 to maintain the rounded proximal end 242 of the impacting rod 244 within the push rod compartment 234. The impacting rod 246 further includes a threaded distal end 254. The impacting rod 246 extends from within the push rod compartment 234 through a bore 252 formed by the outer housing 216.

The outer housing 216 is not used to maintain the push rod 230 properly aligned within the push rod compartment 234 in this embodiment. Rather, the retaining well 244 is used to ensure that the push rod 230 is roughly aligned with the impacting rod 246. Specifically, the push rod 230 is not maintained fixedly against the impacting rod 246 by the biasing spring 232. Thus, if the impacting rod 246 is not mounted to or pressed against another object, then the impacting rod 246 is free to move away from the push rod 230 until the collar 248 rests against the ledge 250 in the outer housing 216. However, the retaining well 244 is configured with walls that are sufficiently high such that even in this condition, the rounded distal end 236 of the push rod 230 will still be within the retaining well 244. Thus, when the push rod 230 and the impacting rod 246 are pressed toward each other, the retaining well ensures that the rounded distal end 236 of the push rod 230 will sufficiently align with the rounded end 242 of the retaining well 244 on the impacting rod 246 to transfer force between the two rods.

The operation of the embodiment of the invention shown in FIG. 7 is similar to the operation of the embodiment of FIG. 2. Initially, the impacting tool 200 is in the condition shown in FIG. 7 with the impacting spring 222 fully extended. Since there is no pressure applied to the contoured handle 202, the biasing spring 232 is also fully extended and the rounded distal end 236 of the push rod 230 is located within the retaining well 244 of the impacting rod 246.

With the biasing spring 232 fully extended, the stem 240 is maintained outside of the central bore 226 of the impacting piston 224. The biasing spring 232 further biases the stem 240 about 10 to 15 degrees off of the centerline of the central bore 226. In this position, the stem 240 is adjacent to a solid portion of the end of the impacting piston 224.

If desired, an impacting tip may be threaded onto the threaded distal end 254. The impacting tool is then positioned such that the impacting tip or threaded distal end 254 is positioned against the component to be impacted. Then, the housing 216 is moved toward the component to be impacted. This causes the contoured handle 202, the impacting spring 222, the impacting piston 224, the biasing spring 232 and the push rod 230 to move toward the component to be impacted. Thus, the rounded distal end 236 of the push rod 230 is forced downward within the retaining well 244 until the rounded distal end 236 contacts the rounded end 242 of the retaining well 244. Proper seating of the rounded distal end 236 and the rounded end 242 is indicated by a rapid increase in resistance.

The impacting tool 200 is then operated by forcing the contoured handle 202 toward the outer housing 216. This causes the impacting spring 222 to be pushed toward the impacting piston 224. If there is any space between the impacting piston 224 and the push rod 230, then the biasing spring 232 is compressed until the impacting piston 224 and the push rod 230 are in physical contact with each other.

Because the proximal end of the stem 240 is not aligned with the central bore 226 of the impacting piston 224, continued pushing on the contoured handle 202 compresses the impacting spring 222. However, unlike the embodiment of FIG. 2, the impacting rod 246 does not necessarily move into the outer housing 216 as the impacting spring 222 is further compressed. Rather, the outer housing 216 may be moved axially either toward or away from the component to be impacted.

If desired, the housing may alternatively be maintained in a fixed relationship to the component to be impacted. This is possible since no portion of the housing is used as a part of the trigger mechanism. Thus, the movement of the housing 216 is only constrained by the distance between the ledge 250 and the collar 248 and/or the position of the stubs 208 and 210 within the grooves 212 and 214. The constraint in this embodiment is that for whatever freedom of movement is desired for the housing, the walls of the retaining well 244 must be high enough to maintain the rounded distal end 236 of the push rod 230 within the well.

Figure 8:
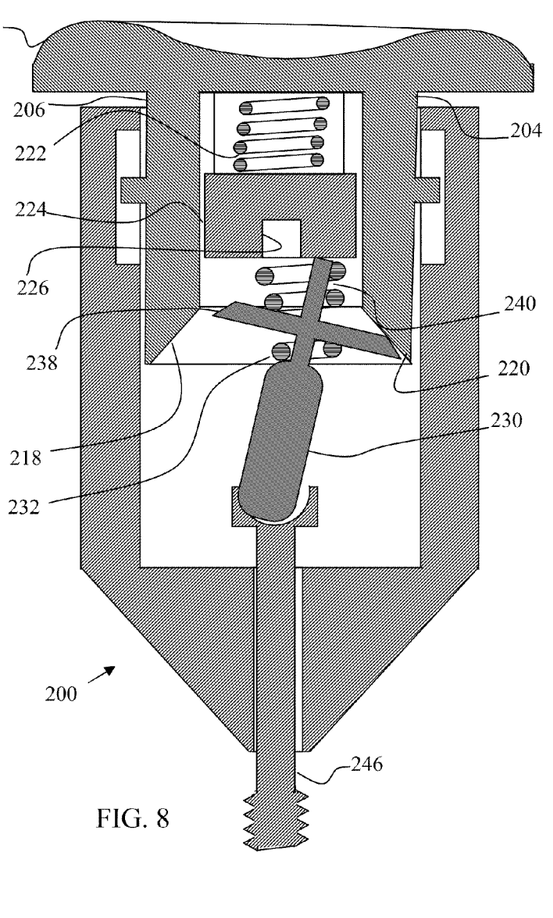
FIG. 8 shows a side cross-sectional view of the impacting tool of FIG. 7 with the impacting spring in a compressed condition.

Continuing with the operation of the impacting tool 200, continued movement of the contoured handle 20 causes the impacting spring 222 to be further compressed and the targeting arms 204 and 206 are forced toward the beveled collar 238 of the push rod 230 until the impacting tool 200 is in the condition shown in FIG. 8.

Figure 9:
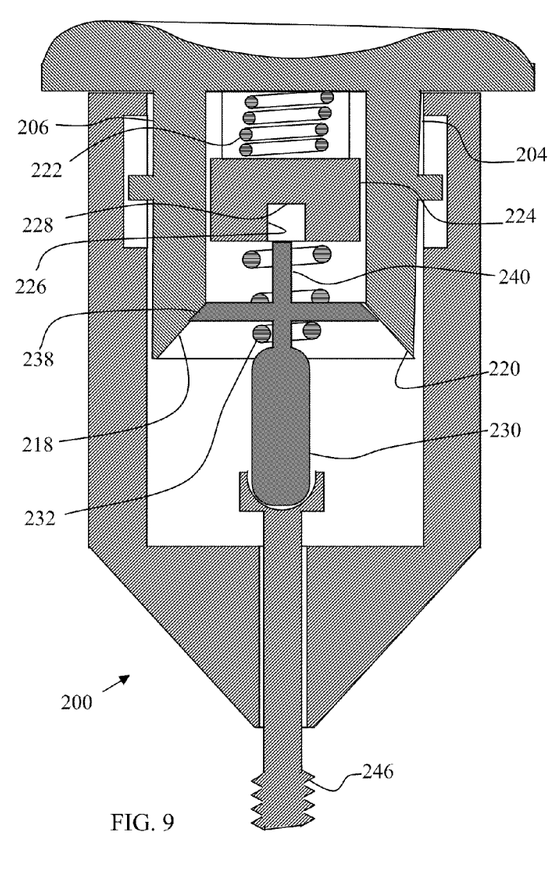
FIG. 9 shows a side cross-sectional view of the impacting tool of FIG. 7 in a triggered condition.

In FIG. 8, the beveled shoulder 220 of the triggering arm 204 is in contact with the beveled collar 238 of the push rod 230. However, the stem 240 is still forced against the impacting piston 224 and the push rod 230 is canted within the push rod compartment 234. The impacting spring 222 is in a compressed condition, with a large amount of energy stored in the impacting spring 222 due to the compression. As the surgeon continues to press upon the contoured handle 202, the beveled shoulder 220 pushes against the beveled collar 238 and the lateral bias of the biasing spring 232 is overcome resulting in lateral movement of the stem 240 toward the center bore 226. As the beveled collar 238 becomes seated against the beveled shoulder 218 of the triggering arm 206 and the beveled shoulder 220 of the triggering arm 204, the stem 240 is brought into alignment with the central bore 226 as shown in FIG. 9.

Since the stem 240 is aligned with the central bore 226 of the impacting piston 224, the impacting tool 200 is in a triggered condition with the impacting spring 222 no longer being forced into compression between the contoured handle 202 and the stem 240. Accordingly, the impacting spring 232 releases the energy stored by compression of the impacting spring 232 and accelerates the impacting piston 224 toward the push rod 230. Thus, in this embodiment, the beveled collar 238 of the push rod 230 in combination with the beveled shoulder 220 comprise a trigger mechanism which may be used to release the energy stored within the impacting spring 232.

Because the stem 240 is longer than the depth of the central bore 226, the first contact between the push rod 230 and the impacting piston 224 occurs when the closed end 228 of the central bore 226 impacts the stem 240. As the closed end 228 of the central bore 226 impacts the stem 240, energy in the form of the momentum of the impacting piston 224 and some residual compression of the impacting spring 232 is transferred to the push rod 230. The energy is in turn transferred to the impacting rod 246 and into the component being impacted.

Of course, in this embodiment the movement of the impacting piston 224 after triggering forces the biasing spring 232 into compression. Therefore, some energy from the impacting spring 222 is absorbed by the biasing spring 232. This cushioning effect is an additional design consideration when selecting, for example, the spring constants of the impacting spring 222 and the biasing spring 232.

After the impact has been delivered, the force being applied to the contoured handle 202 may be released. This allows any remaining compression of the impacting spring 222 and the biasing spring 232 to be released. Thus, the contoured handle 202 is moved axially away from the impacting piston 224 and the biasing spring 232 forces the impacting piston 224 away from the push rod 230. This causes the beveled collar 238 to be moved away from the beveled shoulders 218 and 220 as the triggering arms 204 and 206 are moved with the contoured handle. As the biasing spring 232 decompresses, the impacting piston 224 will be moved such that the stem 240 will be completely outside of the central bore 226 of the impacting piston 224. Since the lateral position of the stem 240 is no longer constrained by the beveled shoulders 218 and 220, the biasing spring 232 forces the stem 240 in a lateral direction, moving the stem 240 out of alignment with the central bore 226 and resetting the impacting tool 200 for another cycle.

Figure 10:
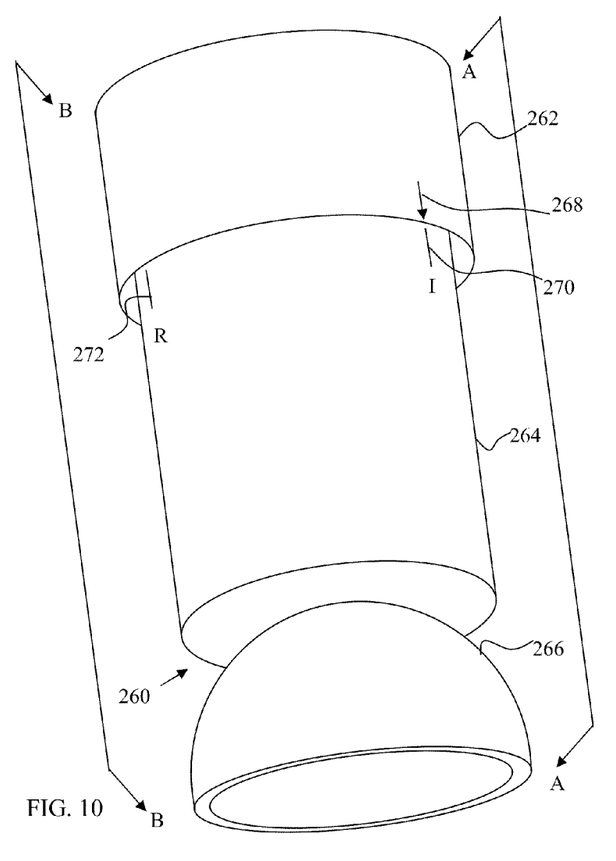
FIG. 10 shows a perspective view of an alternative controlled force impacting tool according to the present invention.

The foregoing embodiments incorporate misalignment of a push rod as part of the trigger mechanism. However, an impacting tool in accordance with the present invention need not rely upon the aligning of a push rod to provide a trigger mechanism. One such impacting tool 260 is depicted in FIG. 10. Impacting tool 260 includes a plunger 262, housing 264 and impacting tip 266. The plunger includes a reference mark 268 that is used in the operation of the impacting tool 260 along with the reference marks 270 and 272 on the housing 264.

Figure 11:
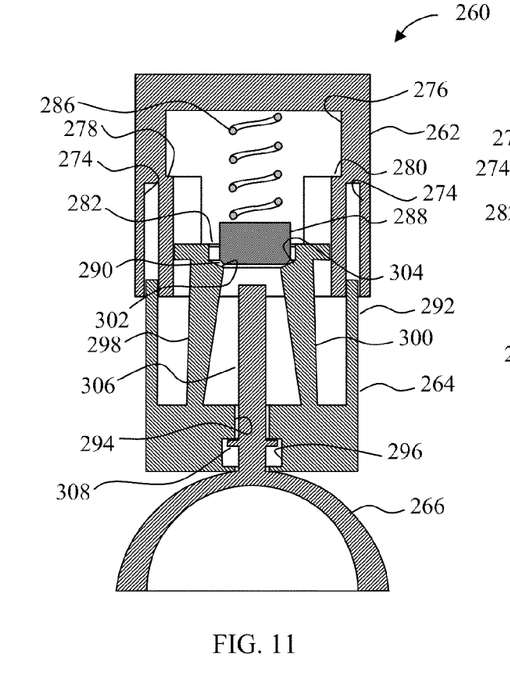
FIG. 11 shows a cross-sectional view of the impacting tool of FIG. 10 taken along the line A-A.

The internals of the impacting tool 260 are shown more fully in FIG. 11 which is a cross section of the impacting tool 260 taken along line A-A of FIG. 10 with the reference mark 268 aligned with the reference mark 270. Thus, FIG. 11 shows the impacting tool configured for impacting as indicated by the "I" adjacent to the reference mark 270.

Figure 12:
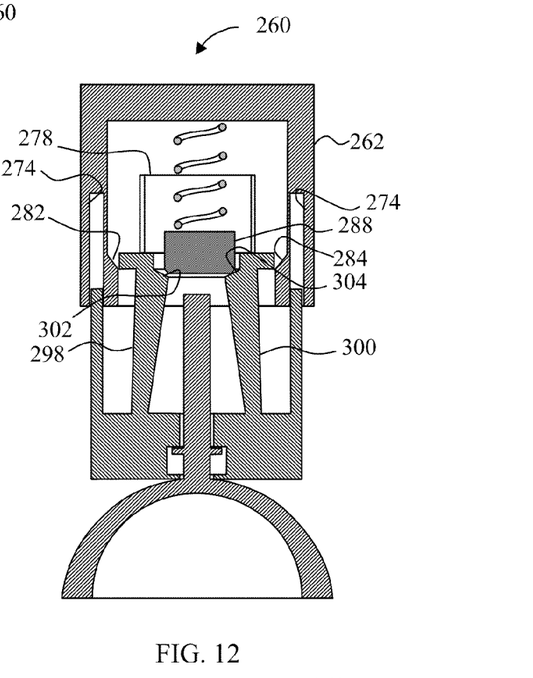
FIG. 12 shows a cross-sectional view of the impacting tool of FIG. 10 taken along the line B-B with the plunger rotated to the reset position.

With reference to FIG. 11, the plunger 262 includes a circumferential slot 274 and an impacting compartment 276. Located within the impacting compartment 276 are two projections 278 and 280 and two ramps 282 and 284. The ramps 282 and 284 are shown more clearly in FIG. 12. FIG. 12 is a cross-section taken along line B-B of FIG. 10, however, for purposes of FIG. 12, the plunger 262 has been rotated such that the reference mark 270 is aligned with the reference mark 272. Thus, FIG. 12 shows the impacting tool configured to be reset as indicated by the "R" next to the reference mark 272.

Continuing with the description of the internals of the impacting tool 260, an impacting spring 286 extends between the upper portion of the plunger 262 and an impacting piston 288. The impacting piston 288 includes a shoulder portion 290 and is located within the impacting compartment 276.

The housing 264 includes an outer wall 292 that is configured to fit within the circumferential slot 274 of the plunger 262. The housing 264 further defines a bore 294 and a compartment 296. Two triggering arms 298 and 300 extend upwardly from the housing 264 into the impacting compartment 276. The triggering arms 298 and 300 include respective shoulder portions 302 and 304. The triggering arms 298 and 300 are sized such that when the plunger 262 is aligned as shown in FIG. 11, the shoulder portion 290 of the impacting piston 288 can contact the shoulder portions 302 and 304 of the triggering arms 298 and 300 but the impacting piston 288 cannot pass between the triggering arms 298 and 300.

The impacting tip 266 is integrally formed with an impacting rod 306. Thus, a kit of impacting tools is contemplated, each with an impacting tip of a different size or configuration. The impacting rod 306 extends through the bore 294 of the housing 264 to a point below the impacting piston 288. The impacting rod includes a collar 308 that is configured to be maintained within the compartment 296 in the housing 264.

In operation, a surgeon or other person first selects the impacting tool with the desired impacting tip 260 for the component to be impacted. For purposes of this example, the impacting tool 260 is already set for impacting. Thus, the plunger 262 is positioned such that the reference mark 268 is aligned with the reference mark 270 and the impacting piston 288 is above the shoulder portions 302 and 304 of the triggering arms 298 and 300 as shown in FIG. 11.

The impacting tip 266 is then placed on the component to be impacted and the plunger 262 is moved toward the component to be impacted. The outer wall 292 of the housing 264 is inserted into the circumferential slot 274 allowing the plunger 262 to be moved toward the impacting tip 266. As the plunger 262 is moved, the shoulder portion 290 of the impacting piston 288 contacts the shoulder portions 302 and 304 of the triggering arms 298 and 300. Because outward movement of the triggering arms 298 and 399 is constrained by the projections 278 and 280, the impacting piston 288 is not allowed to move toward the impacting rod 306. Thus, the impacting spring 286 is compressed.

Figure 13:
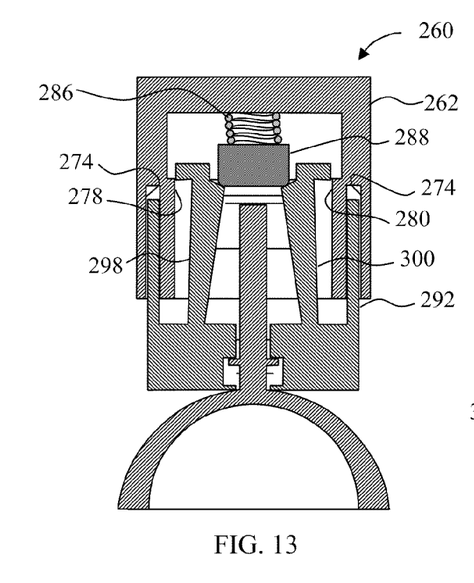
FIG. 13 shows a side cross-sectional view of the impacting tool of FIG. 10 with the impacting spring in a compressed condition.

Continued compression of the impacting spring 286 results in the configuration depicted in FIG. 13. As shown in FIG. 13, the outer wall 292 of the housing 264 is almost completely within the circumferential slot 274 and the triggering arms 298 and 300 have moved upwardly on the projections 278 and 280. The impacting spring 286 is compressed and the impacting piston 288 is being forced by the impacting spring 286 against the triggering arms 298 and 300.

Figure 14:
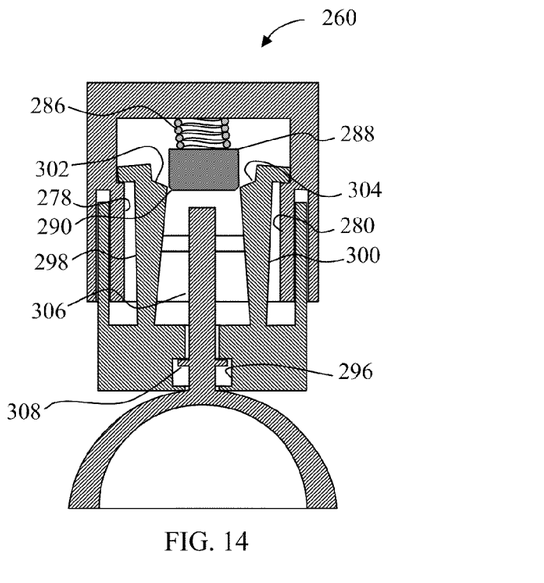
FIG. 14 shows a side cross-sectional view of the impacting tool of FIG. 10 in a triggered condition.
Figures 15, 16, 17:
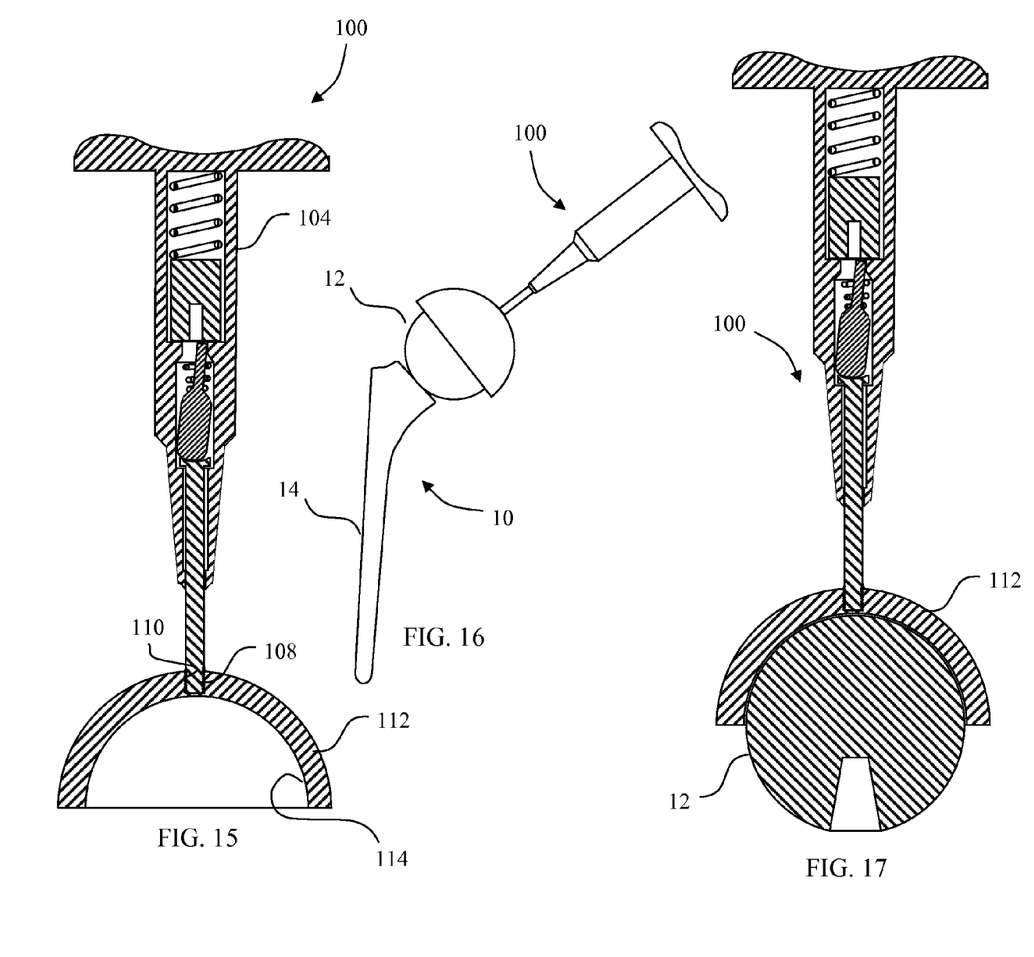
FIG. 15 depicts a cross-sectional view of the impacting tip of FIG. 4 engaged with the controlled force impacting tool of FIG. 2.
FIG. 16 depicts a side plan view of the impacting tip of FIG. 4 positioned on the orthopaedic component of FIG. 1 and engaged with the controlled force impacting tool of FIG. 2
FIG. 17 depicts a cross-sectional view of the impacting tip of FIG. 4 positioned on the femoral head of FIG. 1 and engaged with the controlled force impacting tool of FIG. 2.

Continued movement of the plunger 262 results in the triggering of the impacting tool 260. Specifically, as shown in FIG. 14, the triggering arms 298 and 300 are no longer constrained by the projections 278 and 280. Thus, the shoulder portion 290 of the impacting piston 288 forces the triggering arms 298 and 300 in an outward direction, allowing the impacting piston 288 to move past the shoulder portions 302 and 304 of the triggering arms 298 and 300. Thus, the impacting tool 260 is in a triggered condition, with the triggering arms 298 and 300, the impacting piston 288 and the projections 278 and 280 comprising the triggering mechanism.

Accordingly, the impacting spring 286 releases the energy stored by compression of the impacting spring 286 and accelerates the impacting piston 288 toward the impacting rod 306. The impacting piston 288 then impacts the impacting rod 306 and energy in the form of the momentum of the impacting piston 288 and some residual compression of the impacting spring 286 is transferred to the impacting rod 306. The energy is in turn transferred to the impacting tip 266 and into the component to be, impacted. The compartment 296 allows the collar 308 and thusly the impacting rod 306 to move toward the component being impacted. Of course, the impacting rod and housing may alternatively be integrally formed.

To reset the impacting tool 260, the plunger 262 must first be rotated to align the reference mark 268 with the reference mark 272. Once the plunger 262 has been rotated, the triggering arms 298 and 300 are no longer constrained by the projections 278 and 280. Thus, as shown in FIG. 12, the plunger 262 may be moved away from the impacting tip 266 so as to move the impacting piston 288 above the shoulder portions 302 and 304 of the triggering arms 298 and 300.

Continued movement of the plunger 262 causes the ramps 282 and 284 to move the trigger arms 298 and 300 inwardly, to a position wherein the shoulder portions 302 and 304 of the triggering arms 298 and 300 are underneath the shoulder portion 290 of the impacting piston 288. The ramps 282 and 284 move the triggering arms 298 and 300 inwardly to the same lateral position of the triggering arms 298 and 300 in FIG. 11. Thus, rotation of the plunger 262 so as to align the reference mark 268 with the reference mark 270 causes the triggering arms 298 and 300 to be rotated into position adjacent the projections 278 and 280 as shown in FIG. 11. Accordingly, the impacting tool 260 is reset and ready for the next impacting operation.

Those of ordinary skill in the relevant art will appreciate that the triggering arms 298 and 300 may be designed to have the requisite amount of flexibility for the above described operation by use of materials generally used in the field. Moreover, the triggering arms may alternatively be configured such that the triggering arms resiliently move in the outward direction. In yet another embodiment, the triggering arms may be configured such that the triggering arms resiliently move in the inward direction. These alternative configurations are within the scope of the present invention.

The various impacting tips described above may incorporate alignment aids so as to assist in optimally aligning the impacting tools with the component to be impacted. Such alignment aids may include providing the impacting tip with a key that mates with a corresponding receptacle on the component to be impacted. Alternatively, the impacting tip and component to be impacted may be complimentarily shaped so as to make only when properly aligned. By properly aligning the impacting device, the force needed to either implant a component or to form a Morse tape lock is minimized.

It will be appreciated that the above described embodiments are merely exemplary and that those of ordinary skill in the art may readily devise their own implementations and embodiments that incorporate the principles of the present invention and fall within the spirit and scope thereof. These and other modifications and advantages will become readily apparent to those of ordinary skill in the art and the applicants intend to be bound only by the claims appended hereto.

We claim:

1. A controlled force orthopaedic component impacting kit comprising:

a housing having (i) a distal opening, (ii) a first compartment defining a first ledge at a first distal end thereof, (iii) a second compartment defining a second ledge at a second distal end thereof, (iv) a first passage extending between the distal opening and the first distal end of the first compartment, and (v) a second tapered passage extending between a proximal end of the first compartment and the second distal end of the second compartment and defining an internally tapered wall segment, wherein said first compartment, said second compartment, said first passage, and said second tapered passage collectively define an axis of said housing;

an impacting rod having (i) a proximal rod end portion including a head member defining a first curved surface, said head member being located within said first compartment, (ii) a distal rod end portion defining a first coupling member being located outside of said housing, and (iii) an intermediate rod portion connecting said proximal rod end portion and said distal rod end portion to each other, said intermediate rod portion extending from said first compartment to said outside of said housing through said first passage and said distal opening, wherein said head member is configured to contact said first ledge of said housing during movement of said impacting rod along said axis to maintain said head portion within said first compartment;

a push member located at least partially within said first compartment and configured to extend through said second tapered passage and into said second compartment, said push member having (i) a proximal push member end portion, (ii) a distal push member end portion defining a second curved surface, and (iii) an intermediate push member portion defining an externally tapered wall segment configured to mate with said internally tapered wall segment of said second tapered passage so as to cause said push member to become aligned with said axis during proximal movement of said push member;

a first spring positioned within the first compartment and (i) configured to bias said push member distally so that said second curved surface of said distal push member end portion contacts said first curved surface of said proximal rod end portion within said first compartment, (ii) configured to bias said push member away from alignment with said axis;

a second spring positioned within said second compartment;

an impacting piston positioned within the second compartment between said second spring and said second ledge of said housing, said second spring being configured to bias said impacting piston toward said second ledge, and said impacting piston having a distal piston end portion defining a distal bore configured to receive the proximal push member end portion therein when said externally tapered wall segment of said intermediate push member portion is mated with said internally tapered wall segment of said second tapered passage; and a plurality of impacting tips, each of the plurality of impacting tips (i) including a second coupling member for removably coupling with the first coupling member, and (ii) configured to mate with a respective one of a plurality of orthopaedic components, each of the plurality of orthopaedic components of a size or shape different from the other of the plurality of orthopaedic components.

2. The kit of claim 1, wherein each of the plurality of impacting tips is configured to mate with an orthopaedic component of a size different than each of the other of the plurality of impacting tips.

3. The kit of claim 1, wherein each of the plurality of impacting tips is configured to mate with an orthopaedic component of a shape different than each of the other of the plurality of impacting tips.

4. The kit of claim 3, wherein each of the plurality of impacting tips comprises a curvilinear internal cavity.

5. The kit of claim 4 wherein each of the plurality of impacting tips is configured to mate with the respective orthopaedic component in a single orientation.

6. The kit of claim 5, wherein each of the plurality of impacting tips is configured to mate with a ball portion of an orthopaedic component.

7. The kit of claim 4, wherein the first coupling member is externally threaded.

8. A controlled force orthopaedic component impacting system comprising:

a housing having (i) a distal opening, (ii) a first compartment defining a first ledge at a first distal end thereof, (iii) a second compartment defining a second ledge at a second distal end thereof (iv) a first passage extending between the distal opening and the first distal end of the first compartment, and (v) a second tapered passage extending between a proximal end of the first compartment and the second distal end of the second compartment and defining an internally tapered wall segment, wherein said first compartment, said second compartment, said first passage, and said second passage collectively define an axis of said housing;

an impacting rod having a proximal rod end portion including a head member defining a first curved surface, said head member being located within said first compartment, (ii) a distal rod end portion defining a first coupling member being located outside of said housing, and (iii) an intermediate rod portion connecting said proximal rod end portion and said distal rod end portion to each other, said intermediate rod portion extending from said first compartment to said outside of said housing through said first passage and said distal opening, wherein said head member is configured to contact said first ledge of said housing during movement of said impacting rod along said axis to maintain said head portion within said first compartment;

a push member located at least partially within said first compartment and configured to extend through said second tapered passage and into said second compartment, said push member having (i) a proximal push member end portion, (ii) a distal push member end portion defining a second curved surface, and (iii) an intermediate push member portion defining an externally tapered wall segment configured to mate with said internally tapered wall segment of said second tapered passage so as to cause said push member to become aligned with said axis during proximal movement of said push member;

a first spring positioned within the first compartment and (i) configured to bias said push member distally so that said second curved surface of said distal push member end portion contacts said first curved surface of said proximal rod end portion within said first compartment, (ii) configured to bias said push member away from alignment with said axis;

a second spring positioned within said second compartment;

an impacting piston positioned within the second compartment between said second spring and said second ledge of said housing, said second spring being configured to bias said impacting piston toward said second ledge, and said impacting piston having a distal piston end portion defining a distal bore configured to receive the proximal push member end portion therein when said externally tapered wall segment of said intermediate push member portion is mated with said internally tapered wall segment of said second tapered passage; and at least one impacting tip configured for operable connection to the impacting rod and defining a cavity configured to mate with an orthopaedic component.

9. The controlled force orthopaedic component impacting system of claim 8, wherein the impacting tip is configured to axially align with the axis of a Morse taper member of the orthopaedic component.

10. The controlled force orthopaedic component impacting system of claim 8, wherein:

the at least one impacting tip comprises a plurality of impacting tips, each of the plurality of impacting tips including a second coupling member for removably coupling with the first coupling member.

11. The controlled force orthopaedic component impacting system of claim 10, wherein each of the plurality of impacting tips is configured to mate with an orthopaedic component of a size different than each of the other of the plurality of impacting tips.

12. The controlled force orthopaedic component impacting system of claim 10, wherein each of the plurality of impacting tips is configured to mate with an orthopaedic component of a shape different than each of the other of the plurality of impacting tips.

13. The controlled force orthopaedic component impacting system of claim 12, wherein the first coupling member is externally threaded.

14. The controlled force orthopaedic component impacting system of claim 10, wherein each of the plurality of impacting tips is configured to axially engage a ball portion of the orthopaedic component.

* * * * *